(12) United States Patent
Salisbury et al.

(10) Patent No.: US 9,611,207 B2
(45) Date of Patent: Apr. 4, 2017

(54) RECOVERY OF ACETIC ACID

(71) Applicant: LyondellBasell Acetyls, LLC, Houston, TX (US)

(72) Inventors: Brian A. Salisbury, Beach City, TX (US); Sanjeev Deshpande, Sugar Land, TX (US); Michael E. Fitzpatrick, Nutley, NJ (US); Noel C. Hallinan, Loveland, OH (US); John D. Hearn, Beach City, TX (US)

(73) Assignee: LyondellBasell Acetyls, LLC, Houston, TX (US)

( * ) Notice: Subject to any disclaimer, the term of this patent is extended or adjusted under 35 U.S.C. 154(b) by 0 days.

(21) Appl. No.: 15/007,601

(22) Filed: Jan. 27, 2016

(65) Prior Publication Data
US 2016/0221911 A1    Aug. 4, 2016

Related U.S. Application Data

(60) Provisional application No. 62/110,102, filed on Jan. 30, 2015.

(51) Int. Cl.
| | |
|---|---|
| *C07C 51/12* | (2006.01) |
| *C07C 51/44* | (2006.01) |
| *B01J 31/02* | (2006.01) |
| *B01J 31/10* | (2006.01) |
| *C07C 51/493* | (2006.01) |

(52) U.S. Cl.
CPC ........... *C07C 51/12* (2013.01); *B01J 31/0225* (2013.01); *B01J 31/10* (2013.01); *C07C 51/44* (2013.01); *C07C 51/493* (2013.01); *B01J 2231/49* (2013.01); *Y02P 20/127* (2015.11)

(58) Field of Classification Search
CPC ................................ C07C 51/12; C07C 51/14

USPC ......................................................... 562/519
See application file for complete search history.

(56) References Cited

U.S. PATENT DOCUMENTS

| | | | |
|---|---|---|---|
| 5,599,976 A | * | 2/1997 | Scates ..................... C07C 51/12 562/519 |
| 6,140,535 A | | 10/2000 | Williams |
| 6,153,792 A | * | 11/2000 | Leet ........................ C07C 51/12 560/204 |
| 2008/0033206 A1 | | 2/2008 | Harris et al. |

FOREIGN PATENT DOCUMENTS

| | | |
|---|---|---|
| EP | 849250 A1 | 6/1998 |
| WO | WO-2008016502 A2 | 2/2008 |

OTHER PUBLICATIONS

PCT/US2016/015080 International Search Report and Written Opinion mailed Jun. 23, 2016.

\* cited by examiner

*Primary Examiner* — Sudhakar Katakam
*Assistant Examiner* — Ana Z Muresan

(57) ABSTRACT

The present technology relates to the production and recovery of acetic acid. The recovery processes may include providing a first process stream including acetic acid and greater than 250 ppm of propionic acid; separating at least a portion of the propionic acid from the acetic acid within the first process stream to provide an acetic acid stream including acetic acid and less than 250 ppm of propionic acid and a bottoms stream including propionic acid and acetic acid; reacting the bottoms stream to form a product stream including components of respectively lower boiling points than corresponding components in the bottoms stream; and separating components of the product stream to form an overhead stream including one or more acetates and a bottoms stream including one or more propionates.

20 Claims, 5 Drawing Sheets

RECOVERY OF ACETIC ACID

CROSS-REFERENCE TO RELATED APPLICATIONS

This application claims benefit of priority to U.S. Provisional Application No. 62/110,102 filed on Jan. 30, 2015, which is incorporated herein by reference in its entirety.

BACKGROUND OF THE INVENTION

The present disclosure describes acetic acid production processes. In particular, embodiments discloseded herein relate to the recovery of acetic acid in acetic acid production processes.

Acetic acid production processes include multiple steps for carbonylation reactions and the subsequent recovery of acetic acid. It is a continuous effort in the production of acetic acid to improve the productivity and recover of acetic acid within such processes.

SUMMARY OF THE INVENTION

The present technology relates to processes for producing acetic acid. In one or more embodiments, the processes include contacting methanol, carbon monoxide and optionally methyl acetate in the presence of a reaction medium comprising a carbonylation catalyst under carbonylation conditions sufficient to form a carbonylation product comprising acetic acid; and recovering acetic acid from the carbonylation product. In certain embodiments, the recovery of acetic acid includes flashing the carbonylation product to form a vapor fraction and a liquid fraction; separating components in the vapor fraction to form a first overhead stream, a first acetic acid stream and a first bottoms stream; drying the acetic acid stream to remove water, forming a water stream and a second acetic acid stream; separating components in the second acetic acid stream to form an acetic acid product stream and a second bottoms stream; contacting the second bottoms stream with an alcohol in the presence of an acid catalyst under esterification conditions sufficient to form an esterification product stream comprising alkyl acetate and alkyl propionate; and separating at least a portion of the alkyl acetate from the alkyl propionate within the esterification product stream to form a second overhead stream comprising alkyl acetate and a third bottoms stream comprising alkyl propionate.

In some embodiments, the second acetic acid stream includes from 250 ppm to 2000 ppm propionic acid. In further embodiments, the second acetic acid stream includes 500 ppm or less water. In still further embodiments, the process further includes recycling one or more streams selected from the liquid fraction, the first bottoms stream, the water stream, the second overhead stream and combinations thereof to the carbonylation reaction. In additional embodiments, the acid catalyst is selected from mineral acids, ion exchange resins, acidic zeolites, heteropolyacids and combinations thereof.

In some embodiments, the mineral acids are selected from nitric acid, sulfuric acid, phosphoric acid, hydrochloric acid, methane sulfonic acid, p-toluene sulfonic acid and combinations thereof. In further embodiments, the acid catalyst includes a heterogeneous ion exchange resin. In still further embodiments, the acid catalyst is in liquid phase, soluble solid phase or solid phase. In certain embodiments, 0.01 wt. % to 5 wt. % of the acid catalyst (based on the total weight of acetic acid, acid catalyst and propionic acid) contacts the second bottoms stream. In additional embodiments, the alcohol contacts the second bottoms stream in a molar equivalent of from 1:1 to 9:1 (based on the total molarity of acetic acid and propionic acid). In some embodiments, the alcohol includes an alkyl alcohol such as methanol. In certain embodiments, the second bottoms stream includes from 2 wt. % to 20 wt. % propionic acid.

In some embodiments, the carbonylation conditions include a temperature of from 150° C. to 250° C. and a pressure of from 200 psig (1380 kPa) to 2000 psig (13800 kPa). In further embodiments, the esterification conditions include a temperature of from 30° C. to 80° C. In still further embodiments, alcohol contacts the second bottoms stream within a packed bed reactive distillation column. In certain embodiments, the separating at least a portion of the alkyl acetate from the alkyl propionate within the esterification product stream results in increased efficiency compared to a process absent contacting the second bottoms stream with the alcohol in the presence of an acid catalyst. In additional embodiments, the third bottoms stream includes less than 2 wt. % alkyl acetate.

In one or more embodiments, the process includes providing a first process stream including acetic acid and greater than 250 ppm of propionic acid; separating at least a portion of the propionic acid from the acetic acid within the first process stream to provide an acetic acid product stream including acetic acid and less than 250 ppm of propionic acid and a bottoms stream comprising propionic acid and acetic acid; contacting the bottoms stream with methanol in the presence of an acid catalyst to form a methanolysis product stream including methyl acetate and methyl propionate; and separating at least a portion of the methyl acetate from the methyl propionate within the methanolysis product stream to form an overhead stream including methyl acetate and a bottoms stream including methyl propionate.

In one or more embodiments, the process includes providing a first process stream including acetic acid and greater than 250 ppm of propionic acid; separating at least a portion of the propionic acid from the acetic acid within the first process stream to provide an acetic acid stream including acetic acid and less than 250 ppm of propionic acid and a bottoms stream including propionic acid and acetic acid; reacting the bottoms stream to form a product stream including components of respectively lower boiling points than corresponding components in the bottoms stream; and separating components of the product stream to form an overhead stream including one or more acetates and a bottoms stream including one or more propionates.

While multiple embodiments are disclosed, still other embodiments will become apparent to those skilled in the art from the following detailed description. The embodiments disclosed herein are capable of modifications in various aspects without departing from the spirit and scope of the claims as presented herein. Accordingly, the drawings and detailed description are to be regarded as illustrative in nature and not restrictive.

BRIEF DESCRIPTION OF THE DRAWINGS

The following figures illustrate embodiments of the subject matter disclosed herein. The claimed subject matter may be understood by reference to the following description taken in conjunction with the accompanying figures, in which like reference numerals identify like elements, and in which:

Figure 1:
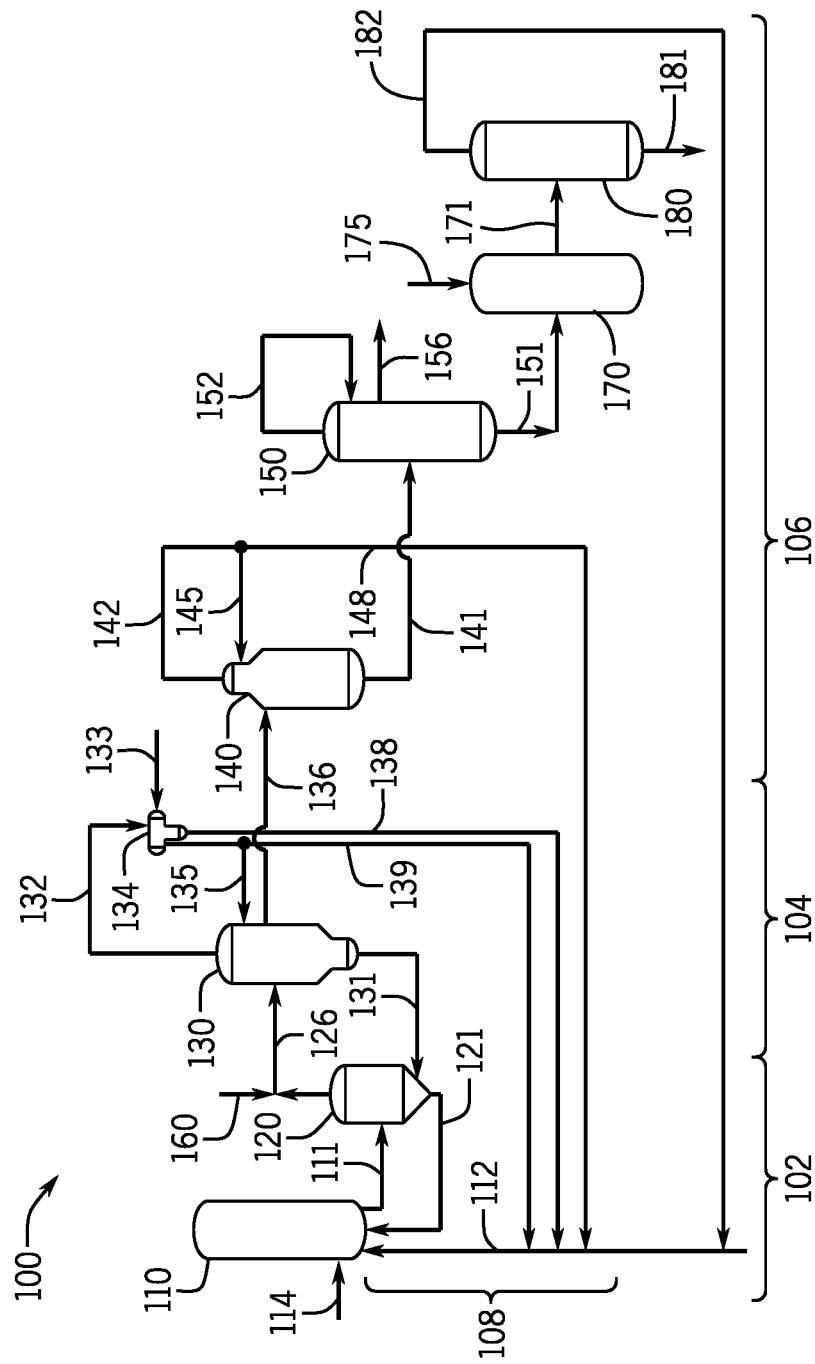
FIG. 1 illustrates a schematic of one or more embodiments of the disclosed process.

While the claimed subject matter may be described using various modifications and alternative forms, the drawings illustrate certain embodiments herein described in detail by way of example. It should be understood, however, that the description herein of specific embodiments is not intended to limit the claimed subject matter to the particular forms disclosed, but on the contrary, the intention is to cover all modifications, equivalents, and alternatives falling within the spirit and scope as defined by the appended claims.

DETAILED DESCRIPTION OF THE INVENTION

Illustrative embodiments of the subject matter claimed below will now be disclosed. In the interest of clarity, not all features of an actual implementation are described in this specification. In the description below, unless otherwise specified, all compounds described herein may be substituted or unsubstituted and the listing of compounds includes derivatives thereof. Furthermore, various ranges and/or numerical limitations may be expressly stated below. It should be recognized that unless stated otherwise, it is intended that endpoints are to be interchangeable. In addition, any ranges include iterative ranges of like magnitude falling within the expressly stated ranges or limitations.

Embodiments described herein include processes for producing carboxylic acids. It will be realized that while specific embodiments herein may refer to acetic acid (often referred to as HOAc) production processes, it is to be understood by one skilled in the art that such embodiments may be utilized in other carboxylic acid production processes. Furthermore, one or more specific embodiments include the production of glacial acetic acid (which is encompassed by the term "acetic acid" as referenced herein). Glacial acetic acid refers to acetic acid that is undiluted (e.g., acetic acid that comprises a water concentration in the parts per million range).

The acetic acid production processes described herein include, but are not limited to carbonylation processes. For example (and for purposes of discussion herein), the acetic acid production processes may include the carbonylation of methanol or its derivatives to produce acetic acid. The embodiments described herein are also applicable to the carbonylation of higher homologues of methanol, such as ethanol, butanol and pentanol, for example, to produce acids which are higher homologues of acetic acid. The adaptation of the embodiments to such systems will be readily apparent to the skilled artisan.

Carbonylation processes may include reacting an alcohol, such as methanol, with carbon monoxide in a liquid reaction medium under carbonylation conditions sufficient to form acetic acid and recovering the acetic acid from the process. Carbonylation processes may optionally include reacting the alcohol with carbon monoxide in the presence of a co-feed, such as an alkyl acetate compound, e.g. methyl acetate.

In some embodiments, the reaction medium includes a carbonylation catalyst. Carbonylation catalysts may include rhodium catalysts, iridium catalysts and/or palladium catalysts. Rhodium catalysts include, but are not limited to rhodium metal and rhodium compounds selected from rhodium salts, rhodium oxides, rhodium acetates, organo-rhodium compounds, coordination compounds of rhodium and mixtures thereof as described, e.g. in U.S. Pat. No. 5,817,869, which is incorporated by reference in its entirety. Iridium catalysts may include iridium metal and iridium compounds selected from acetates, oxalates, acetoacetates and mixtures thereof as described, e.g. in U.S. Pat. No. 5,932,764, which is incorporated by reference in its entirety. The concentration of carbonylation catalyst utilized in the reaction medium may be from 1 mmol to 100 mmol, or from 2 mmol to 5 mmol, or at least 7.5 mmol, or from 2 mmol to 75 mmol, or from 5 mmol to 50 mmol, or from 7.5 mmol to 25 mmol of catalyst per liter of reaction medium. In one or more embodiments, the carbonylation catalyst is utilized with a co-catalyst. The co-catalyst may include metals and metal compounds selected from osmium, rhenium, ruthenium, cadmium, mercury, zinc, gallium, indium, tungsten and mixtures thereof In one or more embodiments, the reaction medium includes from 2 wt. % to 14 wt. %, or 10 wt. % or less, or 8 wt. % or less, or 6 wt. % or less, or from 1 wt. % to 5 wt. %, or from 4 wt. % to 8 wt. % water based on the total weight of the reaction medium. In one or more embodiments, the concentration of water in the reaction medium is referred to as an upstream water concentration. The reaction medium may further include a variety of additives or other components (i.e., components other than the alcohol, carbon monoxide and carbonylation catalyst). The introduction of such additives to the reaction medium can be via any method known in the art. For example, each of the additives may be, either independently or as a mixture, introduced directly to the reaction medium. Alternatively, one or more of the additives may be generated in situ.

The reaction medium may further include an alkyl iodide such as methyl iodide. The concentration of alkyl iodide in the reaction medium may be from 0.6 wt. % to 36 wt. %, or from 4 wt. % to 24 wt. %, or from 6 wt. % to 20 wt. % based on total weight of reaction medium. Furthermore, the reaction medium may include an alkyl acetate such as methyl acetate. The concentration of alkyl acetate in the reaction medium may be from 0.6 wt. % to 36 wt. %, or 2 wt. % to 20 wt. %, or from 2 wt. % to 16 wt. %, or from 3 wt. % to 10 wt. %, or from 2 wt. % to 8 wt. % based on the total weight of the reaction medium. As previously described, the introduction of such components to the reaction medium can be via any method known in the art including introduction directly into the reaction medium or in situ generation. In further embodiments, supplemental hydrogen may be supplied to the reaction medium. Supplemental hydrogen may be supplied to the reaction medium to provide a total hydrogen concentration in the reaction medium from 0.1 mol. % to 5 mol. %, or from 0.3 mol. % to 3 mol. %.

In practice, carbonylation reaction conditions vary depending upon reaction parameters, reactor size and charge and the individual components employed. However, in one or more embodiments, the carbonylation process may be a batch or continuous processes and the carbonylation conditions may include a pressure of from 200 psig (1380 kPa) to 2000 psig (13800 kPa), or from 200 psig (1380 kPa) to 1000 psig (6895 kPa), or from 300 psig (2068 kPa) to 500 psig (3447 kPa), and a temperature of from 150° C. to 250° C., or from 170° C. to 220° C., or from 150° C. to 200° C. Carbonylation processes further include recovering the formed acetic acid from the acetic acid production process. Such recovery can be accomplished by methods that may include separation and/or purification processes. It is to be noted that the discussion of the recovery section includes passing certain streams through various vessels within the recovery section. However, such discussion includes only certain vessels and does not preclude the use of additional vessels and/or processes not discussed herein and known to those skilled in the art. Such additional vessels can be placed wherever desired within the process without altering the fundamental principles discussed herein.

In one or more embodiments, the recovery of the formed acetic acid includes withdrawing a reaction mixture (e.g., a carbonylation product) from the carbonylation reaction. The reaction mixture may include a variety of components, such as acetic acid, methanol, methyl acetate, methyl iodide, carbon monoxide, carbon dioxide, water, and/or hydrogen iodide, among other components. Accordingly, the recovery may include separating components that include but are not limited to separating vapor and liquid components via a reduction in pressure. For example, the flash vessel may include a flash tank, nozzle, valve or combinations thereof. One or more embodiments may include flashing components of the carbonylation product. The "flashing" may include flashing the carbonylation product across a valve to produce a vapor-liquid stream and then separating the vapor from the liquid within a flash vessel to form a liquid fraction and a vapor fraction.

The flash vessel may operate at a pressure below that of the reactor. For example, the flash vessel may operate at a pressure of from 10 psig (70 kPa) to 100 psig (700 kPa), 20 psig (138 kPa) to 90 psig (620 kPa), or from 30 psig (207 kPa) to 70 psig (483 kPa) and a temperature of from 100° C. to 160° C., or from 110° C. to 150° C., or from 120° C. to 140° C. The vapor fraction may include acetic acid and other volatile components, such as methanol, methyl acetate, methyl iodide, carbon monoxide, carbon dioxide, water, hydrogen iodide and combinations thereof as well as impurities, such as propionic acid and acetaldehyde. The liquid fraction may include acetic acid, methanol, methyl acetate, methyl iodide, carbon monoxide, carbon dioxide, water, hydrogen iodide and combinations thereof.

In one or more embodiments, the liquid fraction may be recycled to the carbonylation reaction, while the vapor fraction may be passed to a separation unit (which may include one or more individual units including one or more stages) to form an overhead stream, an acetic acid stream and a bottoms stream. The separation unit may include separation units adapted to provide separation of the higher boiling acetic acid from the lower boiling components, such as methyl iodide and methyl acetate. In one or more embodiments, the separation unit(s) may operate at an overhead pressure of from 20 psia to 40 psia, or 30 psia to 35 psia and an overhead temperature of from 95° C. to 135° C., or from 110° C. to 135° C., or from 125° C. to 135° C. The separation unit(s) may be operated at a bottom pressure of from 25 psia to 45 psia, or from 30 psia to 40 psia and a bottoms temperature of from 115° C. to 155° C., or from 125° C. to 135° C., for example. The overhead stream may include methyl iodide, water methyl acetate, acetic acid, and combinations thereof The bottoms stream may include water, hydrogen iodide, acetic acid, and combinations thereof In one or more embodiments, the bottoms stream may be recycled to the carbonylation reaction.

In some embodiments, the resultant low water concentrations in the reaction mixture can result in inefficient or incomplete separation of the hydrogen iodide and/or iodide from the acetic acid in downstream processes, such as the flash vessel and/or the separation unit(s). In some embodiments, water is added downstream, such as to the separation column, the liquid fraction, or combinations thereof, to provide for efficient separation. Accordingly, upon separation, the acetic acid stream may be passed to a drying column to remove water therefrom, thereby forming a water stream and an acetic acid stream (e.g., a "second acetic acid stream") having a reduce water content. For example, the acetic acid stream withdrawn from the drying column, e.g., the second acetic acid stream, may have 500 ppm or less, or from 200 ppm to 500 ppm water. The drying column may include one or more distillation columns and columns adapted to remove water from the process stream(s) passing therethrough. Drying the acetic acid stream may further include introducing a hydroxide, such as potassium hydroxide or sodium hydroxide, to the drying column. In one or more embodiments, the water stream may be recycled to the carbonylation reaction.

In some embodiments, the recovered acetic acid has a low propionic acid content. However, the acetic acid stream withdrawn from the drying column (e.g., the second acetic acid stream) may have a propionic acid content of at least 250 ppm, or from 250 ppm to 2000 ppm, or from 250 ppm to 1500 ppm. Accordingly, the dried acetic acid stream, such as the second acetic acid stream, may undergo further separation within a separation unit(s), such as those described previously herein, to form an acetic acid product stream and a bottoms stream, such as a second bottoms stream. In some embodiments, the acetic acid product stream has a lower propionic acid content that the second acetic acid stream. For example, the acetic acid product stream may have less than 250 ppm of propionic acid. The second bottoms stream comprises propionic acid and acetic acid. For example, the second bottoms stream may include from 80 wt. % to 98 wt. %, or from 85 wt. % to 95 wt. % acetic acid and from 2 wt. % to 20 wt. %, or from 5 wt. % to 15 wt. %, or from 10 wt. % to 20 wt. % propionic acid. The second bottoms stream may further comprise additional components in minor amounts, such as potassium acetate, other organic compounds and/or low levels of corrosion metals.

In some embodiments, the second bottoms stream is sent to another separation column, such as a "waste acid stripper," to recover as much of the acetic acid as possible and concentrate the propionic acid into a by-product or "waste" stream. The acetic acid recovered via an overhead stream is then recycled back to the carbonylation reaction. However, over time, the waste acid stripper efficiency diminishes and the amount of acetic acid in the waste stream undesirably increases. However, the embodiments described herein provide for improved recovery of acetic acid from the second bottoms stream by reacting the second bottoms stream to form a product stream including components of respectively lower boiling points than corresponding components in the second bottoms stream. Thus, embodiments include contacting the second bottoms stream with an alcohol in the presence of an acid catalyst under esterification conditions sufficient to form an esterification product stream. The alcohol may include those alcohols useful for esterification processes, including alkyl alcohols such as methanol. The esterification product stream includes alkyl acetate and alkyl propionate. When utilizing methanol as the alcohol, the esterification reaction may be referred to interchangeably as methanolysis. In such embodiments, the methanolysis product stream includes methyl acetate and/or methyl propionate.

The acid catalyst may be selected from mineral acids, ion exchange resins, acidic zeolites, heteropolyacids and combinations thereof. In one or more specific embodiments, the acid catalyst includes a heterogeneous ion exchange resin. In additional embodiments, the acid catalyst is in the liquid phase, soluble solid phase or solid phase. As used herein, the terin "mineral acid" refers to any inorganic acid. Non-limiting examples of mineral acids include nitric acid, sulfuric acid, phosphoric acid, hydrochloric acid, methane sulfonic acid, p-toluene sulfonic acid and combinations thereof. Non-limiting examples of ion-exchange resins include strongly acidic ion-exchange resins, such as AMBERLYST™15 Dry, which is a bead form, strongly acidic ion exchange resin developed particularly for heterogeneous acid catalysis for a wide variety of organic reactions. It is available from The Dow Chemical Company. Zeolites constitute a large body of naturally occurring and synthetic aluminosilicate materials that have cationic sites. Varying degrees of proton exchange gives wide to a wide range of zeolite acidity. Non-limiting examples of acid zeolites for use with the embodiments described herein include H-ZSM 5, H-ZSM 22, SAPO-5, Y type zeolites, beta zeolites and combinations thereof Heteropolyacids (HPA's) are a class of complex proton acids formed of a metal, oxygen, an element from the p-block of the periodic table and acidic hydrogen atoms. The hetero atom in an HPA may be selected from copper, beryllium, zinc, nickel, phosphorus, silicon, boron, aluminum, germanium, gallium, iron, cerium, cobalt, arsenic, antimony, bismuth, chromium, tin, titanium, zirconium, vanadium, sulfur, tellurium, manganese, platinum, thorium, hafnium, iodine and combinations thereof The polyatom may be selected from molybdenum, tungsten, vanadium, chromium, niobium, tantalum and combinations thereof. The heteropolyacids may include, but are not limited to, phosphomolybdic acid $(H_3[PO_4(MO_2O_6)_6]xH_2O)$, also known as PMA, tungstosilicic acid $(H_4SiW_{12}O_{40}H_2O)$, also known as TSA, tungstophosphoric acid $(H_3[P(W_3O_{10})_4]xH_2O)$, also known as PTA, molybdosilicic acid $(H_4SiMo_{12}O_{40}xH_2O)$, molybdophosphoric acid $(H_3PMo_{12}O_{40}xH_2O)$, molybdotungstophosphoric acid $(H_3[PMo_nW_{12-n}O_{40}]xH_2O)$, molybdotungstosilicic acid $(H_4[SiMo_nW_{12-n}O_{40}]xH_2O)$, vanadotungstophosphoric acid $(H_{3+n}[PV_nW_{12-n}O_{40}])$, vanadotungstosilicic acid $(H_{4+n}[SiV_nW_{12-n}O_{40}]xH_2O)$, vanadomolybdosilicic acid $(H_{4+n}[SiV_nMO_{12-n}O_{40}]xH_2O)$, vanadomolybdophosphoric acid $(H_{3+n}[PV_nMo_{12-n}O_{40}]xH_2O$, wherein n is an integer of 1 to 11 and x is an integer of 1 or more), tungstoboric acid $(H_5BW_{12}O_{40})$, molybdoboric acid $(H_5BMo_{12}O_{40})$ and molybdotungstoboric acid $(BH_5Mo_6O_{40}W_6)$.

In further embodiments, the heteropolycyclic acid includes a phosphorus or silicon hetero atom and at least one polyatom selected from tungsten, molybdenum, chromium, vanadium, tantalum and combinations thereof. For example, the heteropolyacid may be represented by the formula $H_nM_{12}XO_{40}$, wherein H is hydrogen, M is selected from tungsten and molybdenum, X is selected from phosphorous and silicon and O is oxygen and n is 3 or 4. Non-limiting examples of heteropolyacids include 12-tungstophosphoric acid, 12-tungstosilicic acid, 12-molybdophosphoric acid, 12-molybdosilicic acid and combinations thereof.

The acid catalyst and the alcohol may contact the second bottoms stream in amounts sufficient to form the esterification product stream. For example, the acid catalyst may contact the second bottoms stream in an amount of from 0.01 wt. % to 5 wt. %, or from 0.1 wt. % to 3 wt. %, or from 0.5 wt. % to 2 wt. % (based on the total weight of acid catalyst, acetic acid and propionic acid). The alcohol may contact the second bottoms stream in a molar equivalent of from 1:1 to 9:1, or from 1.5:1 to 5:1, or from 2:1 to 4:1 (based on the total molarity of acetic acid and propionic acid).

Esterification reaction conditions may vary depending upon reaction parameters, reactor size and charge and the individual components employed. However, in one or more embodiments, the esterification process may be a batch or continuous process or processes and the esterification conditions may include a temperature of from 30° C. to 90° C., or from 50° C. to 80 ° C., or from 60 ° C. to 75 ° C. In one or more embodiments, the esterification reaction occurs within a packed bed reactive distillation column. In alternative embodiments, the esterification reaction occurs within a stirred tank reactor.

The resulting lower boiling esters present in the esterification product stream provide for easier separation that those present in the second bottoms stream. As a result, it is expected that the processes of the present technology enhance acetic acid productivity than processes absent the esterification steps described herein. Additional embodiments include separating at least a portion of the alkyl acetate from the alkyl propionate within the esterification product stream to form a second overhead stream and a third bottoms stream. Such separation occurs within a separation unit(s) such as those described herein. The second overhead stream includes alkyl acetate and the third bottoms stream includes alkyl propionate. For example, the third bottoms stream may include less than 2 wt. % alkyl acetate. in one or more embodiments, the second overhead stream may be recycled to the carbonylation reaction.

FIG. 1 illustrates a schematic of an embodiment of an acetic acid production process 100. The various columns and vessels depicted in FIG. 1 may be connected by transfer lines, such as pipes, through with the process solutions flow, such as with the aid of pumps, for example. For ease of depiction and discussion, the transfer lines and streams therein are referred to herein as one in the same, using the term "stream." The process 100 is described in terms of functional areas, i.e., a reaction area 102, a light-ends area 104, a purification area 106 and a recycle area 108, rather than specific process equipment. Note that the "streams" discussed herein may be part of more than one functional area.

The reaction area 102 may include a reactor 110, a flash vessel 120, equipment associated with the reactor 110 and flash vessel 120, and streams associated with the reactor 110 and flash vessel 120. For example, the reaction area 102 may include reactor 110, flash vessel 120, and streams (or portions of streams) 111, 112, 114, 121, 126, 131, 160, 138, 139 and 148. The reactor 110 is a reactor or vessel in which methanol is carbonylated in the presence of a catalyst to form acetic acid at elevated pressure and temperature. The flash vessel 120 is a tank or vessel in which a reaction mixture obtained in the reactor. For example, the reactor 110 is at least partially depressurized and/or cooled to form a vapor stream and a liquid stream.

The light-ends area 104 may include a separations column, for example, a light-ends column 130, equipment associated with light-ends column 130, and streams associated with the light-ends column 130. For example, the light-ends area 104 may include light-ends column 130, decanter 134, and streams 126, 131, 132, 133, 135, 136, 138, 139 and 160. The light-ends column 130 is a fractioning or distillation column and includes any equipment associated with the column, including but not limited to heat exchangers, decanters, pumps, compressors and valves.

The purification area 106 may include a drying column 140, a heavy-ends column 150, equipment associated with drying column 140 and heavy-ends column 150, and streams associated with the drying column 140 and heavy-ends column 150. For example, the purification area 106 may include drying column 140, heavy-ends column 150, and streams 136, 141, 142, 145, 148, 151, 152 and 156. The heavy-ends column 150 is a fractioning or distillation column and includes any equipment associated with the column, including but not limited to heat exchangers, decanters, pumps, compressors and valves. The purification area 106 may further include an esterification zone 170 and a column 180, equipment associated with esterification zone 170 and column 180, and streams associated with esterification zone 170 and column 180. For example, the purification area 106 may include esterification zone 170, column 180, and streams 171, 181 and 182.

The recycle area 108 may include process streams recycled to the reaction area 102 and/or light-ends area 104. For example, in FIG. 1 the recycle area 108 may include streams 121, 138, 139, 148 and 182. In some embodiments, the reactor 110 may be configured to receive a carbon monoxide feed stream 114 and a methanol or methanol/methyl acetate feed stream 112. A reaction mixture may be withdrawn from the reactor in stream 111. Other streams that may be included, such as a stream that may recycle a bottoms mixture of the reactor 110 back into the reactor 110, or a stream may be included to release a gas from the reactor 110. Stream 111 may include at least a part of the reaction mixture.

In certain embodiments, the flash vessel 120 may be configured to receive stream 111 from the reactor 110. In the flash vessel 120, stream 111 may be separated into a vapor stream 126 and a liquid stream 121. The vapor stream 126 may be communicated to the light-ends column 130, and the liquid stream 121 may be communicated to the reactor 110 (stream 121 may thus be considered in the recycle area 108 and in the reactor area 102). In an embodiment, stream 126 may comprise acetic acid, water, methyl iodide, methyl acetate, hydrogen iodide (HI), and mixtures thereof.

In an embodiment, the light-ends column 130 may include a distillation column and equipment associated with the distillation column including but not limited to a heat exchanger 137, a decanter 134, pumps, compressors and valves. The light-ends column 130 may be configured to receive stream 126 from the flash vessel 120. Stream 132 includes overhead product from the light-ends column 130, and stream 131 includes bottoms product from the light-ends column 130. Light-ends column 130 may include a decanter 134, and stream 132 may pass into decanter 134.

Stream 135 may emit from decanter 134 and recycle back to the light-ends column 130. Stream 138 may emit from decanter 134 and may recycle back to the reactor 110 via, for example, stream 112 or be combined with any of the other streams that feed the reactor (stream 138 may thus be considered in the recycle area 108, in the light-ends area 104, and in the reactor area 102). Stream 139 may recycle a portion of the light phase of decanter 134 back to the reactor 110 via, for example, stream 112 (stream 139 may thus he considered in the recycle area 108, in the light-ends area 104, and in the reactor area 102). Stream 136 may emit from the light-ends column 130. Other streams may be included; for example, a stream that may recycle a bottoms mixture of the light-ends column 130 back into the light-ends column 130. Any stream received by or emitted from the light-ends column 130 may pass through a pump, compressor and/or heat exchanger.

In some embodiments, the drying column 140 may comprise a vessel and equipment associated with the vessel including but not limited to heat exchangers, decanters, pumps, compressors and valves. The drying column 140 may be configured to receive stream 136 from the light-ends column 130. The drying column 140 may separate components of stream 136 into streams 142 and 141. Stream 142 may emit from the drying column 140, recycle back to the drying column via stream 145, and/or recycle back to the reactor 110 through stream 148 (via, for example, stream 112). Stream 141 may emit from the drying column 140 and may include de-watered crude acetic acid product. Stream 142 may pass through equipment known in the art, for example, a heat exchanger and/or a separation vessel, before streams 145 or 148 recycle components of stream 142. Other streams may be included; for example, a stream may recycle a bottoms mixture of the drying column 140 back into the drying column 140. Any stream received by or emitted from the drying column 140 may pass through a pump, compressor, heat exchanger and/or separation vessel.

The heavy-ends column 150 may include a distillation column and equipment associated with the distillation column including but not limited to heat exchangers, decanters, pumps, compressors and valves. The heavy-ends column 150 may be configured to receive stream 141 from the drying column 140. The heavy-ends column 150 may separate components from stream 141 into streams 151, 152 and 156. Streams 151 and 152 may be sent to additional processing equipment (not shown) for further processing. Stream 152 may also be recycled, for example, to light-ends column 140. Stream 156 may include acetic acid product.

In certain embodiments, the esterification zone 170 may be configured to receive stream 151 and an alcohol feed stream 175. A reaction mixture may be withdrawn from the esterification zone 170 in stream 171. Esterification zone 170 may further include an acid catalyst disposed therein (not shown). The column 180 may include a distillation column and equipment associated with the distillation column including but not limited to heat exchangers, decanters, pumps, compressors and valves. The column 180 may be configured to receive stream 171 from the esterification zone 170. The column 180 may separate components from stream 171 into streams 181 and 182. Streams 181 and 182 may be sent to additional processing equipment (not shown) for further processing. Stream 182 may also be recycled, in some embodiments, to reactor 110.

EXAMPLES

To facilitate a better understanding of the disclosure, the following non-limiting examples of certain embodiments of the present technology are provided.

Experiments were carried out in 5 mL heavy walled borosilicate septum sealed vials containing 3 mL of solution. Unless stated otherwise, mixtures of methanol and acid catalyst in a septum sealed vial were heated to the desired temperature while the target solution (acetic, propionic or heavy ends bottoms) was heated in a separate vial. At time=0, an aliquot of target solution was injected into the septum sealed vial containing methanol and acid catalyst. The resulting mixture was briefly shaken and subsequently monitored by FTIR by withdrawing samples via syringe at a frequency of 2 minutes or longer. Separate infrared absorbance bands for esters and acids allow for quantitative analysis of decreasing acid concentration and increasing ester concentration.

Figure 2:
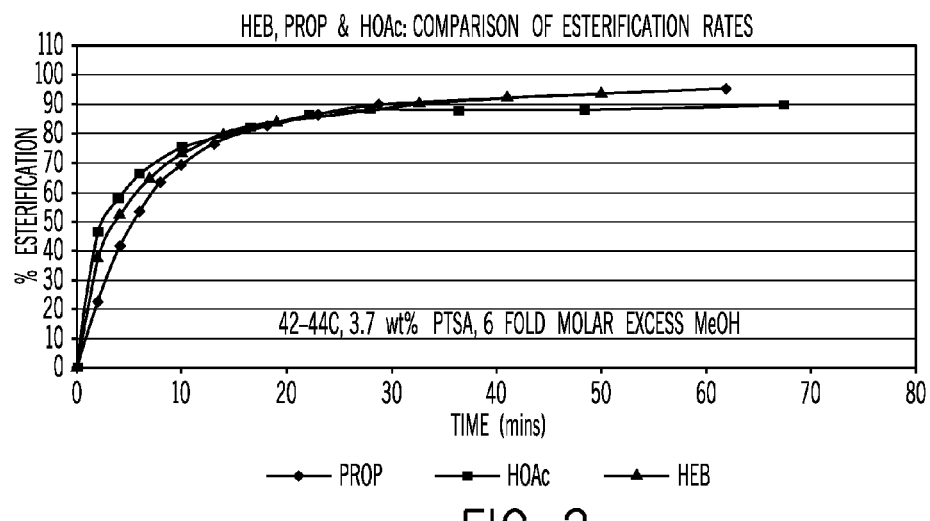
FIG. 2 illustrates esterification time profiles of various samples.

Esterification rates of pure acetic acid, pure propionic acid and a heavy ends bottoms (HEB) sample obtained from a continuous methanol carbonylation process, were measured and compared based on the collected FTIR spectra. The esterification time profiles in FIG. 2 show that rates are very similar with half-lives of only a few minutes under the conditions shown on the plot.

Figure 3:
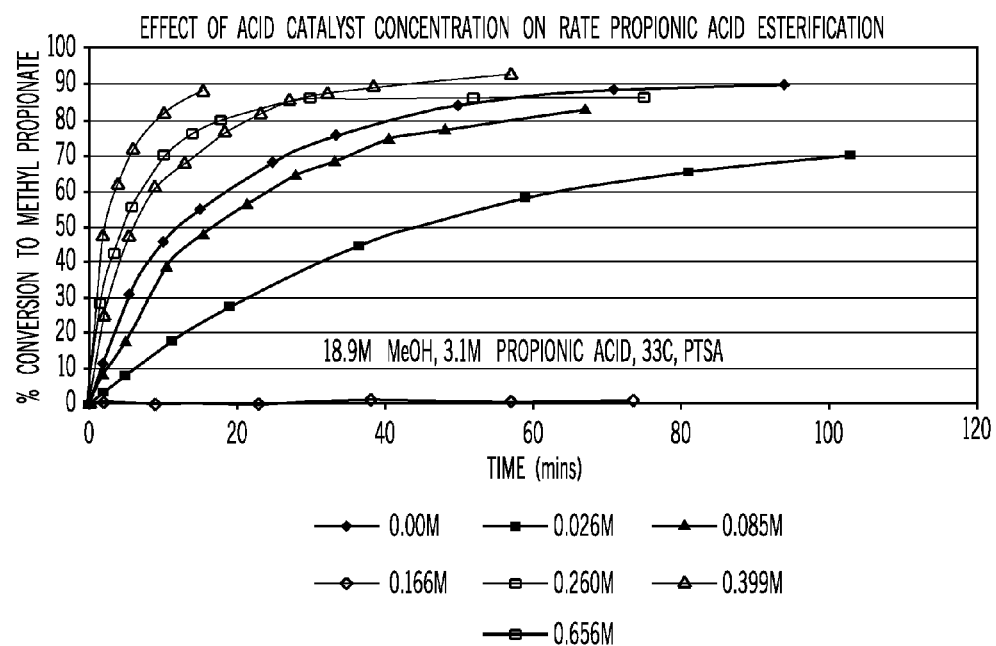
FIG. 3 illustrates esterification plots of various samples.

Subsequent to this verification, the kinetics of acetic and propionic acid esterification were independently investigated to verify that there are no large rate differences that are masked to FTIR in heavy ends bottoms solution. As a first step, the effect of acid catalyst concentration on esterification rate was quantified. In this case, propionic acid was arbitrarily used. The esterification plots in FIG. 3 confirm that esterification does not take place in the absence of an acid catalyst and that the esterification rate increases as para-toluene sulfonic acid (PTSA) concentration is increased from 0.6 wt % (0.026M) to 14 wt % (0.656M).

Figure 4:
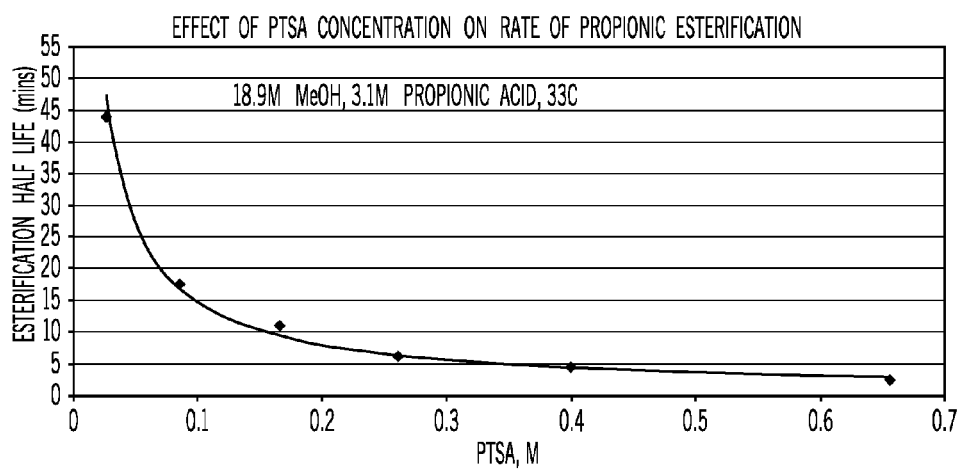
FIG. 4 illustrates esterification half-life plots of various samples.

When esterification half-lives were plotted as shown in FIG. 4, it can be seen that pseudo first order conditions are observed at around 5 wt % PTSA.

Figure 5:
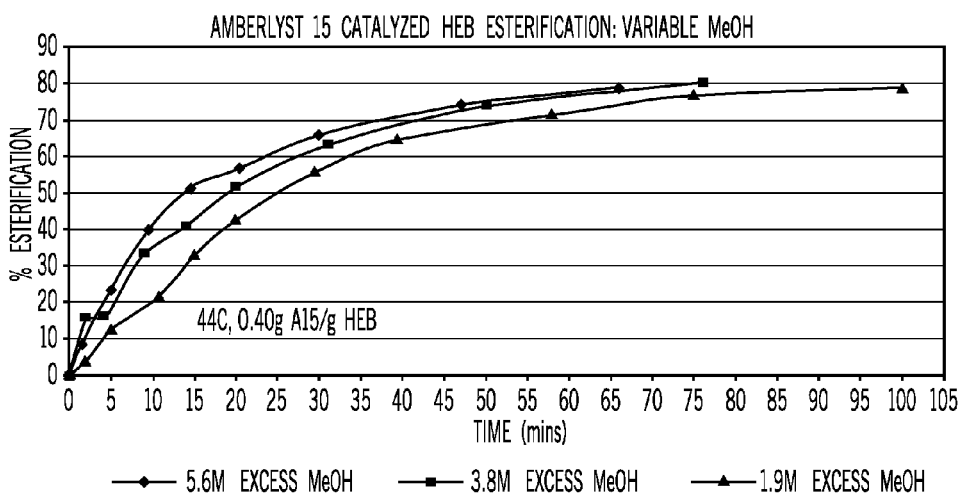
FIG. 5 illustrates reaction profiles of various samples.

As a next step, the reaction order was established. While not limiting the present technology to any particular theory, it was believed that the overall methanolysis reaction is a $3^{rd}$ order reaction with a $1^{st}$ order dependence on each of methanol, carboxylic acid and acid catalyst. As acid catalyst concentration will be invariant in an industrial process, the reaction at constant acid catalyst concentration can be considered to be pseudo-$2^{nd}$ order. At constant acid catalyst concentration, the method of initial rates, which is well known to those skilled in the art of kinetic measurements, was used to determine the order of reaction with regard to reactants, methanol (MeOH) and carboxylic acid. At 44° C. and constant Amberlyst™15 concentration, three runs were carried with MeOH:HEB ratios of 5.6:1, 3.8:1 and 1.9:1. Reaction profiles are shown in FIG. 5.

Simultaneous equations associated with the initial concentrations and initial rates shown in Table 1 were used to determine rate orders.

TABLE 1

| MeOH:HEB | Initial MeOH (M) | Initial HEB (M) | Initial Rate (ms$^{-1}$) |
|---|---|---|---|
| 5.6:1 | 19.75 | 3.5 | $2.06e^{-3}$ |
| 3.8:1 | 17.95 | 4.77 | $1.72e^{-3}$ |
| 1.9:1 | 14.1 | 7.5 | $1.24e^{-3}$ |

44° C., 0.40 g Amberlyst ™ 15/g HEB

Figure 6:
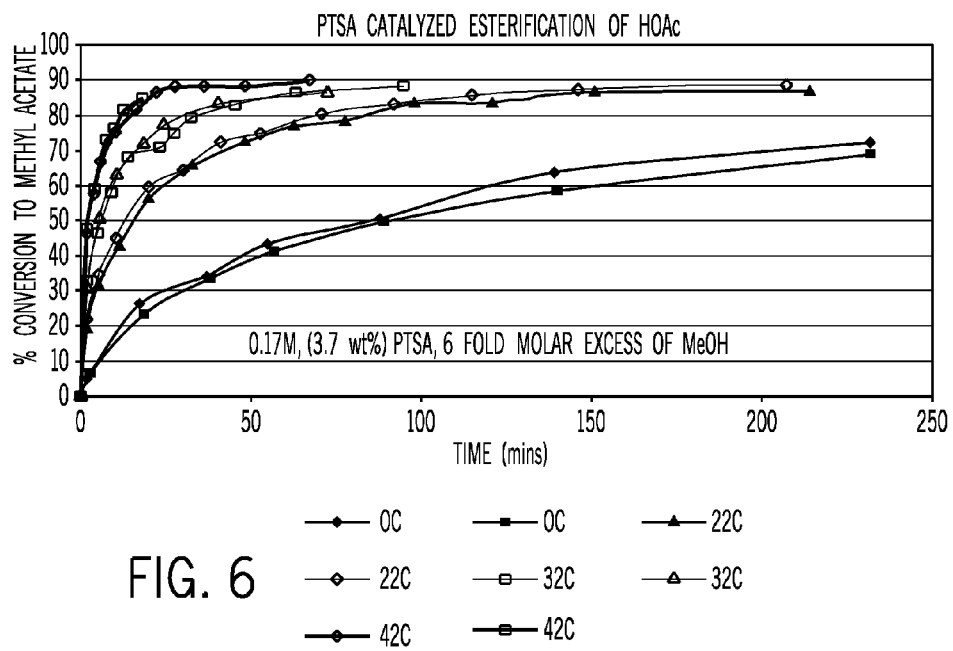
FIG. 6 illustrates time profiles of various samples.
Figure 7:
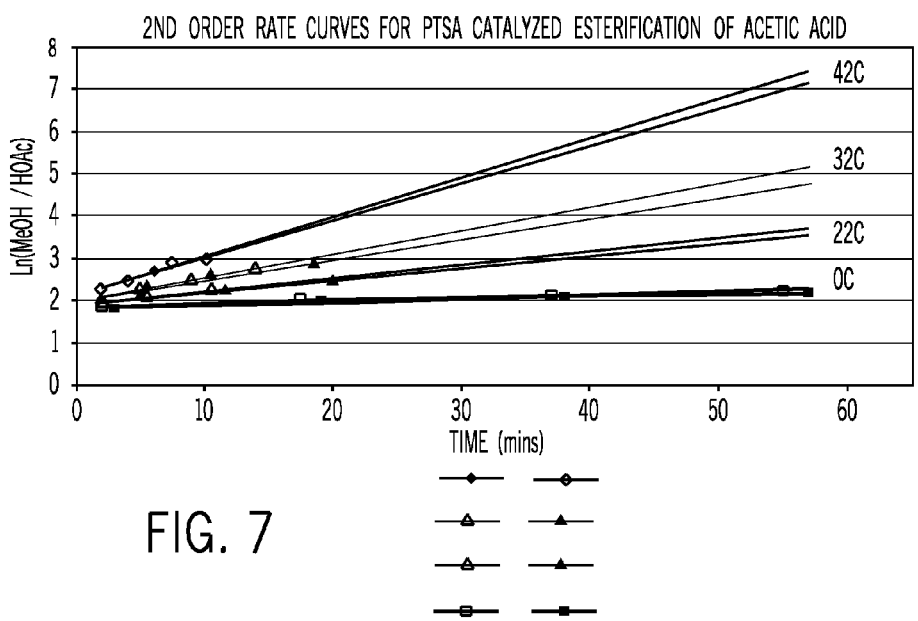
FIG. 7 illustrates second order rate curve plots of various samples.

Experimental values of 1.17 for MeOH and 0.83 for HEB are close enough within the experimental error associated with these fast reactions to the expected values of 1 to confirm that the esterification is $1^{st}$ order in both components. PTSA catalyzed esterification runs were carried out at four different temperatures spanning 0° C.–44° C. for both propionic acid and acetic acid. Duplicate runs were carried out at each temperature. Excellent reproducibility is illustrated in the time profiles for all acetic runs shown in FIG. 6. The corresponding $2^{nd}$ order plots are shown in FIG. 7.

Figure 8:
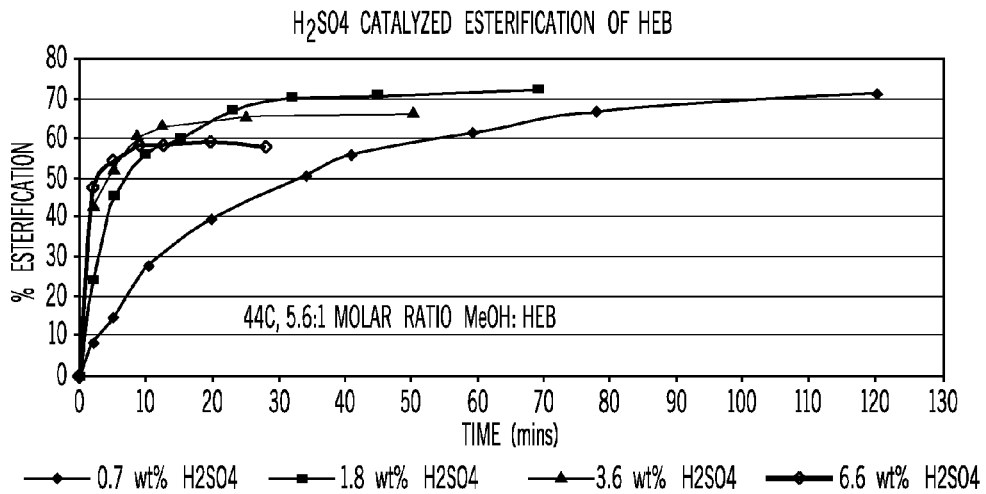
FIG. 8 illustrates time profiles of various samples.

While PTSA was used as the acid catalyst for most of the kinetic studies described above, other homogeneous and heterogeneous acids were also investigated. The effect of variable 96% $H_2SO_4$ concentrations on esterification rate of a plant HEB sample was studied and the time profiles associated with several runs are shown in FIG. 8.

Figure 9:
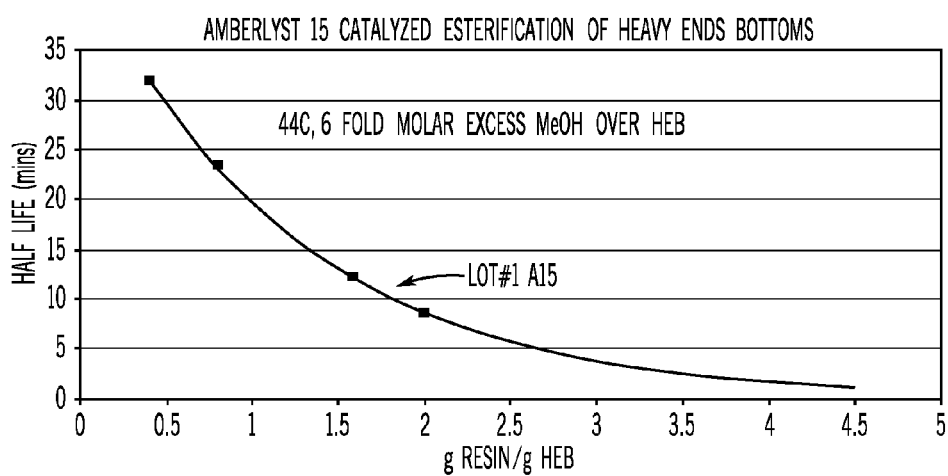
FIG. 9 illustrates esterification profiles of various samples.

Amberlyst™15 was also studied to determine its effectiveness as an acid catalyst and the effect of varying concentrations, which is illustrated in FIG. 9. Good rates were observed and half-lives of only a few minutes were easily achieved under mild conditions.

After analysis of the above studies, it was determined than methanolysis of acetic acid and propionic acid occurs at approximately equal rates with various homogeneous and heterogeneous catalysts. Further, even with competition from the reverse acid catalyzed hydrolysis reaction, the methanolysis reaction can be driven to about 90% completion in static solutions.

Therefore, the embodiments as disclosed herein are well adapted to attain the ends and advantages mentioned as well as those that are inherent therein. The particular embodiments disclosed above are illustrative only, as such they may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined or modified and all such variations are considered within the scope and spirit of the appended claims.

The embodiments illustratively disclosed herein may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. When a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values.

What is claimed is:

1. An acetic acid production process comprising:
    contacting methanol, carbon monoxide and optionally methyl acetate in the presence of a reaction medium comprising a carbonylation catalyst under carbonylation conditions sufficient to form a carbonylation product comprising acetic acid; and
    recovering acetic acid from the carbonylation product, wherein the recovering acetic acid comprises:
        flashing the carbonylation product to form a vapor fraction and a liquid fraction;
        separating components in the vapor fraction to form a first overhead stream, a first acetic acid stream and a first bottoms stream;
        drying the acetic acid stream to remove water therefrom, forming a water stream and a second acetic acid stream comprising 500 ppm or less of water;
        separating components in the second acetic acid stream to form an acetic acid product stream and a second bottoms stream;
        contacting the second bottoms stream with an alcohol in the presence of an acid catalyst under esterification conditions sufficient to form an esterification product stream comprising alkyl acetate and alkyl propionate; and separating at least a portion of the alkyl acetate from the alkyl propionate within the esterification product stream to form a second overhead stream comprising alkyl acetate and a third bottoms stream comprising alkyl propionate.

2. The process of claim 1, wherein the second acetic acid stream comprises from 250 ppm to 2000 ppm propionic acid.

3. The process of claim 1, further comprising recycling one or more streams selected from the liquid fraction, the first bottoms stream, the water stream, the second overhead stream and combinations thereof to the carbonylation reaction.

4. The process of claim 1, wherein the acid catalyst is selected from mineral acids, ion exchange resins, acidic zeolites, heteropolyacids and combinations thereof.

5. The process of claim 4, wherein the mineral acids are selected from nitric acid, sulfuric acid, phosphoric acid, hydrochloric acid, methane sulfonic acid, p-toluene sulfonic acid and combinations thereof.

6. The process of claim 1, wherein the acid catalyst comprises a heterogeneous ion exchange resin.

7. The process of claim 1, wherein the acid catalyst is in liquid phase, soluble solid phase or solid phase.

8. The process of claim 1, wherein from 0.01 wt. % to 5 wt. % acid catalyst (based on the total weight of acetic acid, acid catalyst and propionic acid) contacts the second bottoms stream.

9. The process of claim 1, wherein the alcohol contacts the second bottoms stream in a molar equivalent of from 1:1 to 9:1 (based on the total molarity of acetic acid and propionic acid).

10. The process of claim 1, wherein the alcohol comprises methanol.

11. The process of claim 1, wherein the second bottoms stream comprises from 2 wt. % to 20 wt. % propionic acid.

12. The process of claim 1, wherein the carbonylation conditions comprise a temperature of from 150° C. to 250° C. and a pressure of from 200 psig (1380 kPa) to 2000 psig (13800 kPa).

13. The process of claim 1, wherein the esterification conditions comprises a temperature of from 30° C. to 80° C.

14. The process of claim 1, wherein alcohol contacts the second bottoms stream within a packed bed reactive distillation column.

15. The process of claim 1, wherein the third bottoms stream comprises less than 2 wt. % alkyl acetate.

16. An acetic acid separation process comprising:
providing a first process stream comprising acetic acid and greater than 250 ppm of propionic acid;
separating at least a portion of the propionic acid from the acetic acid within the first process stream to provide an acetic acid product stream comprising acetic acid, less than 500 ppm of water and less than 250 ppm of propionic acid and a bottoms stream comprising propionic acid and acetic acid;
contacting the bottoms stream with methanol in the presence of an acid catalyst selected from mineral acids, ion exchange resins, acidic zeolites, heteropolyacids and combinations thereof to form a methanolysis product stream comprising methyl acetate and methyl propionate; and
separating at least a portion of the methyl acetate from the methyl propionate within the methanolysis product stream to form an overhead stream comprising methyl acetate and a bottoms stream comprising methyl propionate.

17. The process of claim 16, wherein the mineral acids are selected from nitric acid, sulfuric acid, phosphoric acid, hydrochloric acid, methane sulfonic acid, p-toluene sulfonic acid and combinations thereof.

18. An acetic acid separation process comprising:
providing a first process stream comprising acetic acid and greater than 250 ppm of propionic acid;
separating at least a portion of the propionic acid from the acetic acid within the first process stream to provide an acetic acid stream comprising acetic acid, less than 500 ppm of water and less than 250 ppm of propionic acid and a bottoms stream comprising propionic acid and acetic acid;
reacting the bottoms stream to form a product stream comprising components of respectively lower boiling points than corresponding components in the bottoms stream; and
separating components of the product stream to form an overhead stream comprising one or more acetates and a bottoms stream comprising one or more propionates.

19. The process of claim 18, wherein the reacting comprises contacting the bottoms stream with methanol in the presence of an acid catalyst acid catalyst selected from mineral acids, ion exchange resins, acidic zeolites, heteropolyacids and combinations thereof at a concentration of 0.01 wt. % to 5 wt. % acid catalyst (based on the total weight of acetic acid, acid catalyst and propionic acid) to form the product stream comprising methyl acetate and methyl propionate.

20. The process of claim 1, wherein the second acetic acid stream comprises 200-500 ppm of water.

* * * * *

UNITED STATES PATENT AND TRADEMARK OFFICE
CERTIFICATE OF CORRECTION

PATENT NO. : 9,611,207 B2  
APPLICATION NO. : 15/007601  
DATED : April 4, 2017  
INVENTOR(S) : Brian A. Salisbury et al.

Page 1 of 1

It is certified that error appears in the above-identified patent and that said Letters Patent is hereby corrected as shown below:

In the Drawings

| | | |
|---|---|---|
| Sheet 5 of 5, Fig. 8 | Line 1 | Delete "H2SO4" and insert --$H_2SO_4$-- |
| Sheet 5 of 5, Fig. 8 | Line 12 | Delete "H2SO4" and insert --$H_2SO_4$-- |
| Sheet 5 of 5, Fig. 8 | Line 12 | Delete "H2SO4" and insert --$H_2SO_4$-- |
| Sheet 5 of 5, Fig. 8 | Line 12 | Delete "H2SO4" and insert --$H_2SO_4$-- |
| Sheet 5 of 5, Fig. 8 | Line 12 | Delete "H2SO4" and insert --$H_2SO_4$-- |

In the Specification

| | | |
|---|---|---|
| Column 1 | Line 13 | Delete "discloseded" and insert --disclosed-- |
| Column 4 | Line 25 | After "thereof", insert --.-- |
| Column 5 | Line 30 | Delete "liquid." and insert --liquid-- |
| Column 5 | Line 64 | After "thereof", insert --.-- |
| Column 5 | Line 66 | After "thereof", insert --.-- |
| Column 6 | Line 55 | Delete "improved." and insert --improved-- |
| Column 7 | Line 10 | Delete "terin" and insert --term-- |
| Column 7 | Line 26 | After "thereof", insert --.-- |
| Column 7 | Line 35 | After "thereof", insert --.-- |
| Column 7 | Line 47 | Delete "($H_{3+n}[PV_nW_{12-n}O_{40}]$)," and insert --($H_{3+n}[PV_nW_{12-n}O_{40}]$),-- |
| Column 8 | Line 33 | Delete "in" and insert --In-- |
| Column 9 | Line 63 | Delete "he" and insert --be-- |
| Column 10 | Line 35 | Delete "140." and insert --130.-- |

Signed and Sealed this  
Twenty-second Day of October, 2019

Andrei Iancu  
*Director of the United States Patent and Trademark Office*